(12) United States Patent
Tabuchi

(10) Patent No.: US 8,336,150 B2
(45) Date of Patent: Dec. 25, 2012

(54) TREATMENT TOOL

(75) Inventor: Yasuhiro Tabuchi, Tokyo (JP)

(73) Assignee: Olympus Medical Systems Corp. (JP)

( * ) Notice: Subject to any disclaimer, the term of this patent is extended or adjusted under 35 U.S.C. 154(b) by 35 days.

(21) Appl. No.: 12/797,028

(22) Filed: Jun. 9, 2010

(65) Prior Publication Data
US 2011/0028787 A1    Feb. 3, 2011

Related U.S. Application Data

(63) Continuation of application No. PCT/JP2009/070570, filed on Dec. 8, 2009.

(30) Foreign Application Priority Data

Dec. 9, 2008    (JP) ................................ P2008-313485

(51) Int. Cl.
*B08B 9/04* (2006.01)
(52) U.S. Cl. .......................................... 15/104.2; 15/106
(58) Field of Classification Search ............... 15/104.05, 15/104.09, 105.095, 104.16, 104.2, 106, 15/164
See application file for complete search history.

(56) References Cited

U.S. PATENT DOCUMENTS

| | | | |
|---|---|---|---|
| 189,455 A * | 4/1877 | Hamilton .......................... 403/66 |
| 810,913 A * | 1/1906 | Coleman ....................... 15/104.2 |
| 2,544,847 A * | 3/1951 | Malesky .................. 15/104.165 |
| 2,739,368 A | 3/1956 | McCall | |
| 4,399,627 A * | 8/1983 | Malesky et al. .................... 42/95 |
| 4,997,419 A | 3/1991 | Lakatos et al. .................. 604/55 |
| 5,005,943 A | 4/1991 | Fort | |
| 5,168,593 A | 12/1992 | Poje et al. | |
| 5,253,386 A * | 10/1993 | LaLonde .......................... 15/206 |
| 5,297,310 A * | 3/1994 | Cox et al. ......................... 15/106 |
| D414,610 S * | 10/1999 | Davila ............................. D4/138 |
| 6,210,330 B1 | 4/2001 | Tepper .......................... 600/439 |
| 2008/0141473 A1 | 6/2008 | Arai et al. | |
| 2008/0281153 A1 | 11/2008 | Nakamura et al. | |

(Continued)

FOREIGN PATENT DOCUMENTS

GB    818278    8/1959

(Continued)

OTHER PUBLICATIONS

Search Report issued Jan. 26, 2010 in connection with corresponding application No. PCT/JP2009/070570.

(Continued)

*Primary Examiner* — Mark Spisich
(74) *Attorney, Agent, or Firm* — Ostrolenk Faber LLP

(57) ABSTRACT

Provided is a treatment tool including: an elongated member which is formed of a flexible material and includes first and second terminals; a first body portion which is fixed to the first terminal so as to function in a target; a handle portion which is provided in the second terminal and is provided with a rotating holding portion holding the elongated member so as to be rotatable about the axis of the elongated member; and a second body portion which is attached to the handle portion so as to function in a target and is rotated relative to the elongated member when rotating the handle member relative to the elongated member. The treatment tool is capable of performing a cleaning treatment or the like while curtailing extraneous matter from being scattered in the vicinity thereof and reducing contamination thereof.

6 Claims, 10 Drawing Sheets

U.S. PATENT DOCUMENTS

2008/0301894 A1    12/2008    Wang

FOREIGN PATENT DOCUMENTS

| | | |
|---|---|---|
| JP | 61-163523 | 10/1986 |
| JP | 01-101915 | 4/1989 |
| JP | 3-018345 | 1/1991 |
| JP | 03-018345 | 1/1991 |
| JP | 07-000345 | 1/1995 |
| JP | 2003-506129 | 2/2003 |
| JP | 2004-016504 | 1/2004 |
| JP | 2006-175170 | 7/2006 |
| JP | 3144106 | 7/2008 |
| JP | 2008-284317 | 11/2008 |

OTHER PUBLICATIONS

Office Action issued by Japanese Patent Office on Nov. 24, 2010 in connection with corresponding Japanese application No. 2010-2010-522042 and English translation thereof.

Office Action issued by Japanese Patent Office on Nov. 24, 2010 in connection with corresponding Japanese application No. 2010-522042 and English translation thereof.

Notice of Allowance mailed by Japanese Patent Office on Feb. 22, 2011 in connection with corresponding Japanese application No. 2010-522042 and English translation thereof.

International Search Report and Written Opinion mailed Jan. 26, 2010 in corresponding PCT International Application No. PCT/JP2009/070570.

Search Report issued by European Patent Office and received by applicant on Apr. 16, 2012 in connection with corresponding EP patent application No. EP 09 83 1912.

Search Report issued by European Patent Office and received by applicant on Apr. 17, 2012 in connection with corresponding EP patent application No. EP 09 83 1912.

\* cited by examiner

TREATMENT TOOL

Priority is claimed on Japanese Patent Application No. 2008-313485, filed Dec. 9, 2008, and this application is a continuation application based on PCT/JP2009/70570. The content is incorporated herein by reference.

BACKGROUND OF THE INVENTION

1. Field of the Invention

The present invention relates to a treatment tool that is used in an endoscope.

2. Description of the Related Art

For some time, an endoscope has been being provided with fluid conduits such as a suction conduit and a water/air supply conduit used to ensure an field of view when observing the inside of a body cavity. In such conduits, patient's blood, viscous fluid, bodily secretion, and the like may pass therethrough when performing an examination or surgery using an endoscope. In addition, such liquids and the like may flow reversely into the conduits from the opening portion of the front end of the endoscope, and such liquids and the like may remain inside the conduits even after the examination. For this reason, a treatment of cleaning out the liquids and the like adhering to the inner walls of the conduits using a brush is performed.

As an example of the treatment tool used in the endoscope, JP-A-2006-175170 discloses a cleaning brush used in the endoscope. The brush disclosed in the patent document includes a shaft which is elongated and flexible and a brush portion which includes brush bristles for cleaning the inside of the conduit and is formed in the front end of the shaft. Further, the patent document discloses a cleaning brush assembly to which an opening brush is detachably fixed so as to clean the opening portion of the conduit of the endoscope as well as the cleaning brush (brush portion) for the conduit of the endoscope.

According to the cleaning brush assembly, it is possible to provide both the conduit cleaning brush and the opening brush.

SUMMARY OF THE INVENTION

An object of the present invention is to provide a treatment tool capable of further improving the workability of the treatment.

In order to achieve the above-described object, the present invention proposes the following means.

A treatment tool of the present invention includes: an elongated member which is formed of a flexible material and includes first and second terminals; a first body portion which is fixed to the first terminal so as to function in a target; a handle portion which is provided in the second terminal and is provided with a rotating holding portion holding the elongated member so as to be rotatable about the axis of the elongated member; and a second body portion which is attached to the handle portion so as to function in a target and is rotated relative to the elongated member when rotating the handle member relative to the elongated member.

According to the treatment tool of the present invention, when the handle portion is rotated about the axis, the handle portion is rotated about the axis along with the connection portion. Accordingly, the second body portion fixed to the connection portion is rotated along with the connection portion, but the elongated member rotatably locked to the connection portion is not interlocked with the rotation operation of the connection portion. Therefore, the first body portion fixed to the first terminal of the elongated member is not interlocked with the rotation operation of the handle portion, and is not moved by the rotation of the handle portion. As a result, it is possible to further improve the workability of the treatment.

Further, in the treatment tool of the present invention, the second terminal may include a swollen portion which is swelled in the radial direction of the elongated member, and the handle portion may include a concave portion to which the swollen portion is fitted so as to be rotatable about the axis.

In this case, the swollen portion is provided in the elongated member, and is fitted to the concave portion provided in the connection portion. Accordingly, it is possible to simply form the swollen portion and the concave portion.

Further, in the treatment tool of the present invention, the second terminal may include a contraction portion which is formed in a part of the outer peripheral surface of the second terminal so as to have a diameter smaller than those of the other portions, and the handle portion may include a support portion which slidably engages with the contraction portion and supports the elongated member so as to be rotatable about the axis.

In this case, since the support portion of the connection portion supports the contraction portion provided in the outer peripheral surface of the second terminal, the rotation operation of the second terminal is freely performed with respect to the connection portion, and the forward/backward movement is regulated. Accordingly, since a free running distance of the handle portion is shortened with respect to the elongated member when moving the first body portion forward or backward while gripping the handle portion, it is possible to appropriately move the first body portion forward or backward.

Further, in the treatment tool of the present invention, the handle portion may include an expansion portion which is enlarged in the radial direction of the elongated member.

In this case, since the handle portion is enlarged in the radial direction of the elongated member, it is possible to rotate the second body portion with a small force while gripping the outer peripheral surface of the handle portion.

Further, in the treatment tool of the present invention, the handle portion may include a convex protrusion portion which protrudes outward from the outer peripheral surface of the handle portion and extends in parallel to the axis.

In this case, since the operator's fingers are locked to the convex protrusion portions provided on the outer peripheral surface of the handle portion, it is possible to prevent the sliding movement on the handle portion using the convex protrusion portions. As a result, it is possible to reliably rotate the handle portion.

Further, in the treatment tool of the present invention, the handle portion may include a grip surface which is formed in a part of the outer peripheral surface of the handle portion so as to be formed as a plane parallel to the axis.

In this case, since the operator's fingers are locked to the grip surface provided on the outer peripheral surface of the handle portion, it is possible to prevent the sliding movement on the handle portion using the grip surface. As a result, it is possible to reliably rotate the handle portion.

Further, the treatment tool of the present invention may further include a fluid conduit which circulates a fluid between the first and second body portions.

In this case, a fluid supply source is connected to any one of the portions on the side of the first and second body portions in the fluid conduit, and the other thereof is guided to the treatment target. Accordingly, it is possible to supply a fluid to the treatment target from the fluid supply source. Therefore, since the first body portion and the second body portion are relatively rotatable about the axis of the elongated member, it is possible to improve the operability of the treatment tool while the elongated member is not twisted.

Further, in the treatment tool of the present invention, the first body portion may include a brush which is capable of scraping the inside of a tube.

In this case, the brush of the first body portion is capable of removing extraneous matter adhering to the inner peripheral surface of the tube while scraping the inside of the tube.

Further, in the treatment tool of the present invention, the second body portion may include a brush which is capable of scraping the inside of a tube.

In this case, the brush of the second body portion is capable of removing extraneous matter adhering to the inner peripheral surface of the tube while scraping the inside of the tube. In addition, even when the handle portion is rotated, since the second terminal of the elongated member is rotatable, it is possible to suppress the first body portion from being rotated while being interlocked with the rotation operation of the handle portion.

Further, a treatment tool of the present invention includes: an elongated member which includes first and second terminals; a first body portion which is fixed to the first terminal; a connection portion which is locked to the second terminal so as to be rotatable about the axis of the elongated member; and a second body portion which is fixed to the connection portion and extends in the axial direction of the elongated member, wherein the connection portion includes a handle portion which rotates the second body portion about the axis of the elongated member, and wherein the second body portion includes a brush capable of scraping the inside of a tube.

DETAILED DESCRIPTION OF THE INVENTION

First Embodiment

Hereinafter, a treatment tool according to a first embodiment of the present invention will be described with reference to FIGS. 1 to 4.

Figure 1:
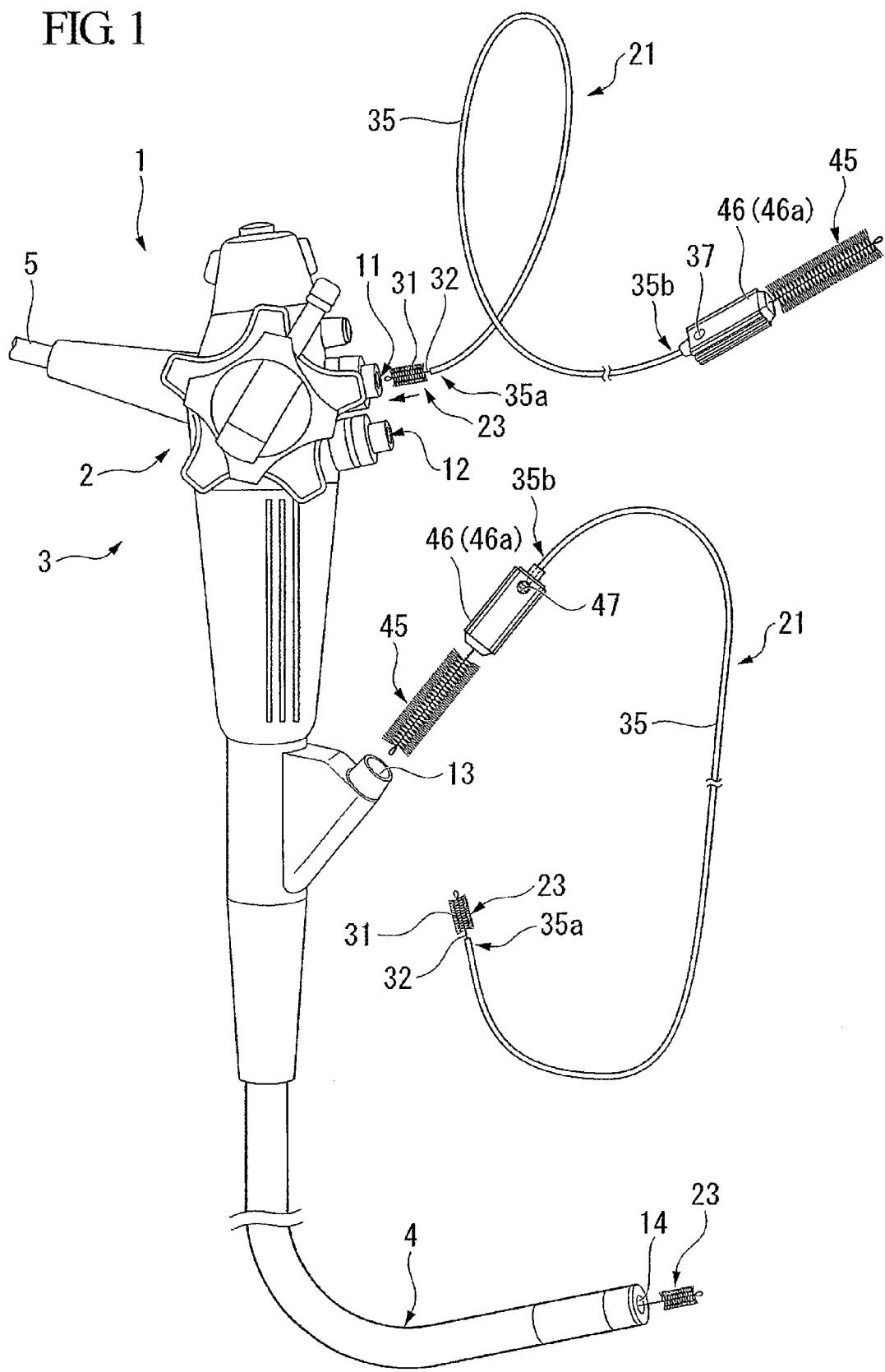
FIG. 1 is a perspective view illustrating an endoscope as a treatment target and a treatment tool according to a first embodiment of the present invention.

FIG. 1 is an entire view illustrating an endoscope 1 as a cleaning treatment target of the embodiment. The endoscope 1 includes a manipulation portion 3 which is provided with a manipulation knob 2 and the like; an insertion unit 4 which has flexibility and is inserted into a body cavity; and a universal cord 5 which includes a light guide and the like to be connected to a light source device (not shown).

The endoscope 1 of the present invention includes a suction conduit 11; a water/air supply conduit 12; a forceps insertion opening 13 which is an example of an opening portion; and the like. The front end portion of the insertion unit 4 is provided with an opening portion 14 which is used as a forceps opening or a suction opening. In order to clean the inside of the suction conduit 11, the inside of the water/air supply conduit 12, and the like, a treatment tool 21 of the present invention is used.

In addition, the treatment tool 21 of the present invention is provided with an elongated member 35 that includes a first terminal 35a and a second terminal 35b. The elongated member 35 is formed in a tube shape or a string shape having flexibility, and may desirably have elasticity.

Further, the first terminal 35a is provided with a first body portion 23. The first body portion 23 is provided with a brush shaft 32 which is formed of a stranded string and is provided to mainly clean the inner wall of the suction conduit 11, the water/air supply conduit 12, or the conduit from the forceps insertion opening 13 to the opening portion 14; and a plurality of brush bristles 31 which protrudes from the brush shaft 32 to the outside in the radial direction of the brush shaft 32. The brush shaft 32 is formed of stainless steel and has elasticity.

Figure 2:
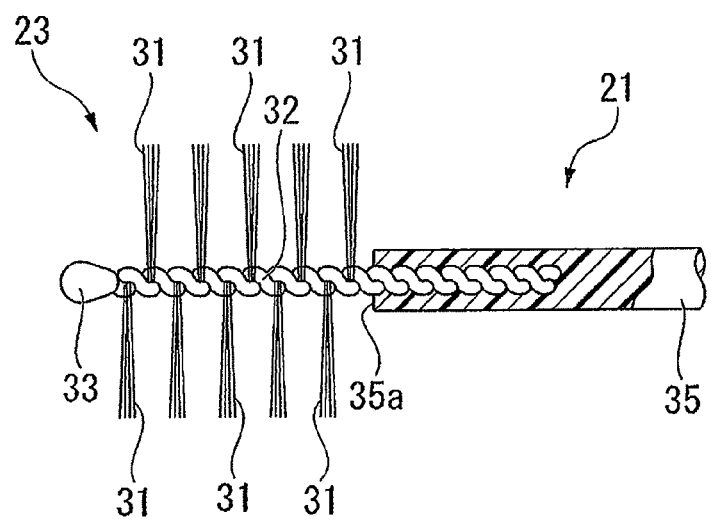
FIG. 2 is a side view illustrating a configuration of a part of a first terminal of the treatment tool when viewed from a part of the section thereof.

As shown in FIG. 2, one end of the brush shaft 32 is threaded into the end surface of the first terminal 35a of the elongated member 35 so as to be attachably/detachably fixed thereto. In addition, since the brush shaft 32 is adapted to be attachable to or detachable from the elongated member 35, the brush shaft may be separately discarded after the treatment tool 21 is used, however the brush shaft 32 and the elongated member 35 may be fixed to each other by adhering or welding.

The other end of the brush shaft 32 coaxially extends from the first terminal 35a of the treatment tool, and a front end cap 33 is fixed thereto. The front end cap 33 is used to prevent the brush shaft 32 from contacting a cleaning target, and to prevent the cleaning target from being damaged.

In addition, the brush bristles 31 are formed of several bound resin fibers and are disposed and inserted in the brush shaft 32 with a predetermined interval therebetween. The fixation of the brush bristles 31 to the brush shaft 32 is performed by a pressing force generated when twisting the brush shaft 32.

The length of the brush bristles 31 may be appropriately selected depending on the cleaning target, and may be equal to or larger than a half of the inner diameter of the cleaning target.

Figure 3:
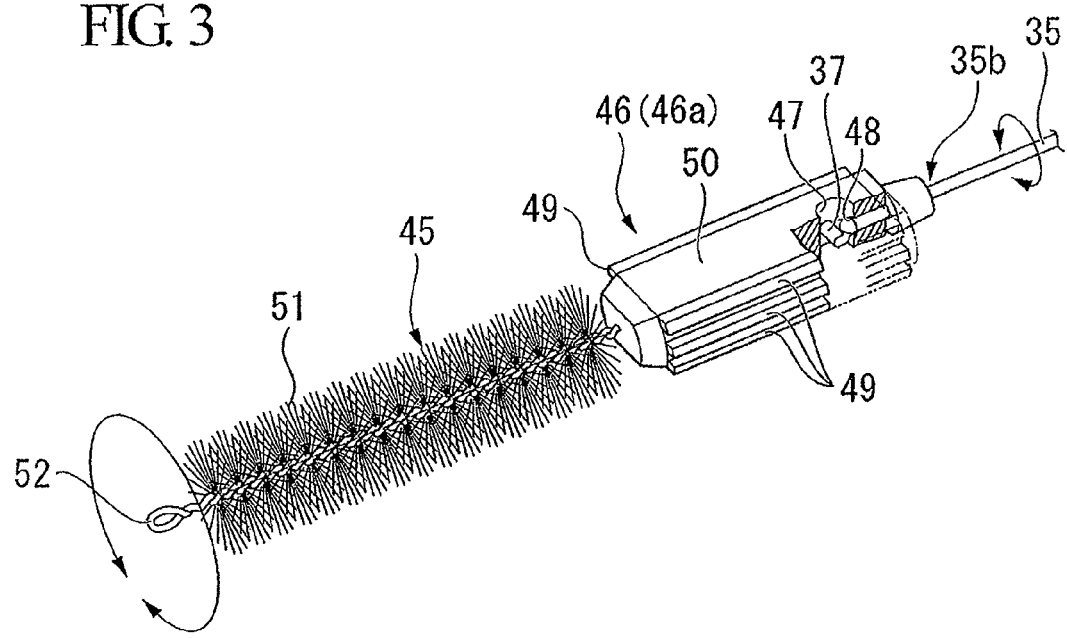
FIG. 3 is a perspective view illustrating a configuration of a part of the treatment tool.

As shown in FIG. 3, a substantially tubular connection portion 46 is locked to the second terminal 35b of the elongated member 35. The connection portion 46 is provided with a rotation shaft 48 which is formed in the axial direction to have a diameter larger than the outer diameter of the elongated member 35; and a concave portion 47 which is recessed to intersect the rotation shaft 48.

The second terminal 35b of the elongated member 35 is inserted into the rotation shaft 48, and its outer peripheral surface is heated and compressed in two directions facing each other in the radial direction in the concave portion 47. The second terminal 35b is elevated in a direction perpendicular to the above-described compression direction, and is formed as a swollen portion 37 that is larger than the inner diameter of the rotation shaft 48. The swollen portion 37 is used to restrict the forward/backward movement of the elongated member 35 with respect to the connection portion 46 by being brought into contact with the inner wall surface of the concave portion 47 and the opening end portion of the rotation shaft 48.

In addition, a second body portion 45 is fixed to the end surface facing the rotation shaft 48 in the connection portion 46. The second body portion 45 is provided to mainly clean the forceps insertion opening 13 (refer to FIG. 1) of the endoscope 1, and is formed in a brush shape similarly to the first body portion 23. The second body portion 45 is provided with a brush shaft 52 which is formed of a stranded string; and a plurality of brush bristles 51 which protrudes from the brush shaft 52 to the outside in the radial direction.

Further, one end of the brush shaft 52 is threaded and fixed to the connection portion 46, and is disposed to be coaxial or substantially coaxial with the rotation shaft 48. As in the first body portion 23, the brush shaft 52 may be adapted to be attachable thereto or detachable therefrom so as to be separately discarded later.

Furthermore, in the embodiment, the brush shaft 52 is folded back at the middle portion thereof, and is twisted with the brush bristles 51 interposed therebetween. Even in the second body portion 45, the front end cap having the same configuration as that of the front end cap 33 may be adopted.

Moreover, the brush bristles 51 may be formed of the same resin as that of the brush bristles 31, but their length is appropriately selected in accordance with the inner diameter of the cleaning target (the forceps insertion opening 13 and the like) to be cleaned.

Besides, the outer peripheral surface of the connection portion 46 is formed as an expansion portion that is larger than any one of the elongated member 35 and the brush shaft 52 in the radial direction, and serves as a handle portion 46a that is gripped by an operator. In addition, the handle portion 46a is provided with grip surfaces 50 which face each other in the radial direction and each has an outer peripheral surface partially cut in a plane shape.

Further, the connection portion 46 is provided with a plurality of convex protrusion portions 49 which is provided between the grip surfaces 50 in the circumferential direction of the connection portion 46 and extends in parallel to the axis of the connection portion 46. In the embodiment, a group is formed by three convex protrusion portions 49 that are disposed at the same interval in the circumferential direction, and altogether six convex protrusion portions are so disposed opposite each other in the radial direction.

The operation of the treatment tool of the embodiment having the above-described configuration will be described with reference to FIGS. 1 to 4. First, in the endoscope 1 to be subjected to a cleaning treatment, for example, the cleaning treatment performed on the suction conduit 11 shown in FIG. 1 will be described.

As shown in FIG. 1, the operator inserts the first body portion 23 of the elongated member 35 into the opening on the side of the manipulation portion 3 of the suction conduit 11 while gripping the outer peripheral surface in the vicinity of the first body portion 23. Subsequently, the operator presses the elongated member 35 while gripping the outer peripheral surface of the elongated member 35 until the first body portion 23 protrudes from the opening portion 14 of the front end of the endoscope 1.

The brush bristles 31 provided on the first body portion 23 scrape the inner wall of the conduit so that biological tissue adhering to the inner wall of the conduit are entangled in the interstices of the brush bristles 31. When the first body portion 23 protrudes from the opening portion 14, the operator immerses the brush bristles 31 into cleaning liquid (water, chemical liquid, or the like), and removes the above-described extraneous matter while holding and washing the brush bristles 31 using his/her fingers.

Subsequently, the operator extracts the first body portion 23 from the manipulation portion 3 in the endoscope 1 while gripping the handle portion 46a. Here, the brush bristles 31 scrape the inner wall of the conduit in a direction opposite to the above-described direction so as to further entangle biological tissue adhering to the inner wall of the conduit.

When the first body portion 23 is extracted from the forceps insertion opening 13, the operator immerses the brush bristles 31 in cleaning liquid in the same way as described above, and removes the extraneous matter while holding and washing the brush bristles 31.

As described above, the operator cleans the inner wall of the conduit by repeating the insertion/extraction operation of the first body portion 23.

Subsequently, the operator cleans the inlet of the conduit, for example, the forceps insertion opening 13 and the opening portion 14. Hereinafter, an exemplary case of cleaning the forceps insertion opening 13 will be described.

Figure 4:
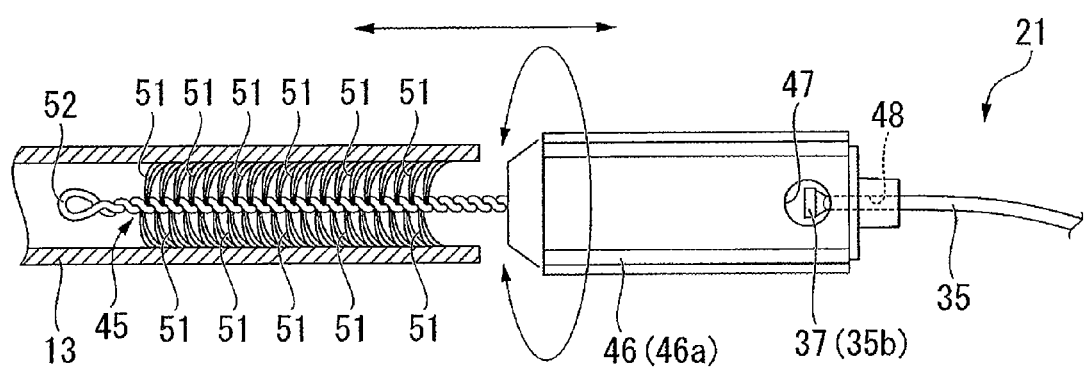
FIG. 4 is an explanatory diagram illustrating an operation when the treatment tool is used.

As shown in FIG. 4, the operator inserts the second body portion 45 into the forceps insertion opening 13 by a predetermined depth while gripping the handle portion 46a. For example, in the embodiment, the second body portion 45 is inserted until colliding with the inside of the forceps insertion opening 13. Here, the brush bristles 51 scrape the inner peripheral surface of the forceps insertion opening 13 in the axial direction so as to entangle extraneous matter adhering to the inner peripheral surface of the forceps insertion opening 13.

Subsequently, the operator rotates the handle portion 46a once in the circumferential direction. Then, the brush bristles are rotated once in the circumferential direction along with the handle portion 46a, and scrape the inner peripheral surface of the forceps insertion opening 13 while rotating in the circumferential direction so as to entangle the extraneous matter.

The elongated member 35 is curved and dropped in the vertical direction due to its own weight and the weight of the first body portion 23. In the connection portion 46, the connection portion 46 rotates in the circumferential direction, that is, a direction about the brush shaft 52 and the rotation shaft 48 in accordance with the rotation operation of the handle portion 46a. Since the elongated member 35 is rotatable about the rotation shaft 48, the elongated member 35 slides inside the rotation shaft 48 in accordance with the rotation of the connection portion 46. As a result, the rotation operation of the connection portion 46 is not transmitted to the elongated member 35.

Accordingly, when the handle portion 46a is rotated once in the circumferential direction, only the second body portion 45 is rotated once in the circumferential direction along with the rotation of the connection portion 46.

Subsequently, the operator extracts the second body portion 45 from the forceps insertion opening 13. Then, the brush bristles 51 axially scrape the inner wall of the forceps insertion opening 13 in a direction opposite to the insertion direction of the second body portion 45 so as to entangle the extraneous matter adhering to the inner wall of the forceps insertion opening 13.

After the second body portion 45 is extracted from the forceps insertion opening 13, the operator holds and washes the brush bristles 51 in the same way of holding and washing the brush bristles 31.

The operator performs the cleaning operation until the extraneous matter adhering to the inner peripheral surface of the forceps insertion opening 13 is totally removed by repeating the inserting, rotating, extraction, and holding/washing for the forceps insertion opening 13.

When the cleaning operation is completed, the treatment tool 21 is discarded in accordance with a predetermined rule, and the series of operation ends.

As described above, according to the treatment tool 21 of the embodiment, it is possible to clean the inner wall surface of the tube-shaped member, that is, the inside of the conduit connected from the forceps insertion opening 13 to the opening portion 14 by the use of the first body portion 23 provided in the first terminal 35a of the elongated member 35. Further, it is possible to clean the inner peripheral surface of the forceps insertion opening 13 by the use of the second body portion 45 rotatably connected via the connection portion 46.

In addition, even when the second body portion 45 is rotated while gripping the handle portion 46a, the elongated member 35 slides around the rotation shaft 48. As a result, the elongated member 35 is not interlocked with the rotation operation, and the first body portion 23 does not move before or after the rotation operation. Accordingly, it is possible to further improve the workability of the treatment.

Further, even when the second body portion 45 is rotated, the first body portion 23 does not rotate. Accordingly, it is possible to curtail the extraneous matter adhering to the first body portion 23 from scattering.

Furthermore, since the swollen portion 37 is formed by heating and pressing the second terminal 35b of the elongated member 35, it is possible to manufacture the treatment tool simply and to decrease the manufacturing cost thereof.

Moreover, since the convex protrusion portions 49 are provided on the outer peripheral surface of the handle portion 46a so as to protrude outward in the radial direction, it is possible to efficiently transfer a force of rotating the second body portion 45.

Second Embodiment

Next, a treatment tool according to a second embodiment of the present invention will be described with reference to FIGS. 5 and 6. Further, in the respective embodiments to be described below, the same reference numerals will be given to the same components as those of the treatment tool of the first embodiment, and the description thereof will be omitted.

Figure 5:
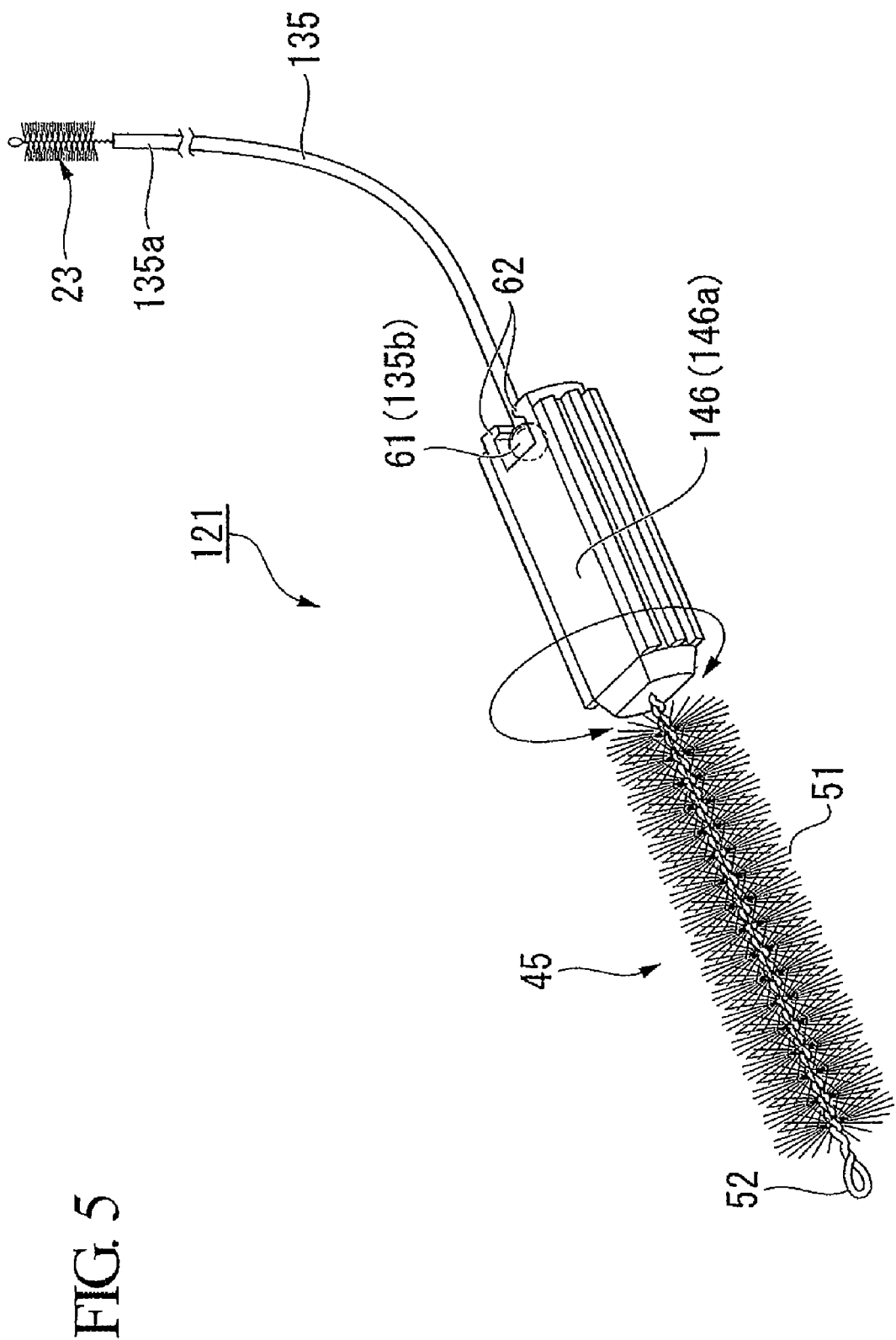
FIG. 5 is a perspective view illustrating a treatment tool according to a second embodiment of the present invention.
Figure 6:
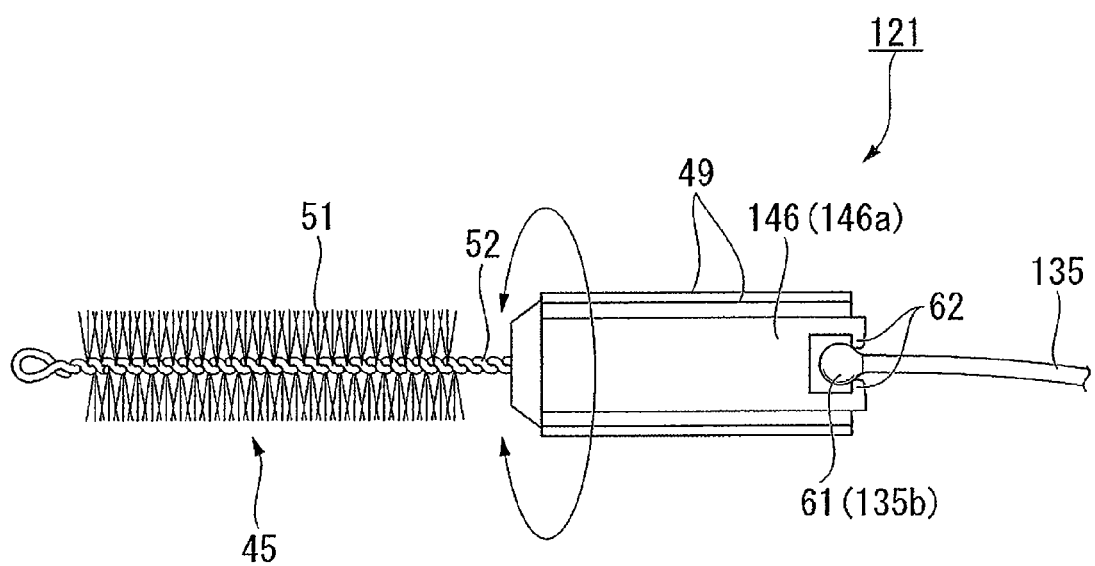
FIG. 6 is a side view illustrating a configuration of a part of the treatment tool.

As shown in FIGS. 5 and 6, the embodiment is different from the first embodiment in that a treatment tool 121 includes a connection portion 146 instead of the connection portion 46, and includes an elongated member 135 instead of the elongated member 35.

A second terminal 135b of the elongated member 135 is provided with a substantially spherical swollen portion 61 which is equally elevated from the axis of the elongated member 135 to the outside in the radial direction. In addition, the connection portion is provided with a support portion 62 that supports the second terminal 135b instead of the rotation shaft 48 of the first embodiment. The support portion 62 surrounds the outer periphery of the swollen portion 61 so as to be covered by the swollen portion 61.

In addition, the connection portion 146 is formed of a resin having elasticity, and the support portion 62 is pressed against the outer peripheral surface of the swollen portion 61 to be elastically deformed when the swollen portion 61 is pulled or pressed toward the first terminal 135a by a force exceeding a predetermined force. That is, the connection portion 146 and the elongated member 135 are attachable to each other or detachable from each other by moving the connection portion 146 forward or backward and the elongated member 135 in the axial direction.

Further, the connection portion 146 is provided with the convex protrusion portions 49 as described above, and the connection portion 146 includes a handle portion 146a that is used by the operator to grip and manipulate the first body portion 23 or the second body portion 45.

Even in such a configuration, the elongated member 135 is rotatable about the axis of the elongated member 135 while being supported on the support portion 62, and the rotation operations of the connection portion 146 and the elongated member 135 are not interlocked with each other. For this reason, as in the first embodiment, even when the handle portion 46a is rotated while extraneous matter such as biological tissue adheres to the first body portion 23, it is possible to rotate the second body portion 45 without scattering the extraneous matter from the first body portion 23.

Further, since the elongated member 135 and the connection portion 146 are adapted to be attachable to each other or detachable from each other, it is possible to easily assemble the treatment tool 121.

Third Embodiment

Next, a treatment tool according to a third embodiment of the present invention will be described with reference to FIGS. 7 to 10.

The embodiment is different from the above-described embodiments in that a treatment tool 221 includes a connection portion 246 instead of the connection portion 46, and includes an elongated member 235 instead of the elongated member 35.

Figure 7:
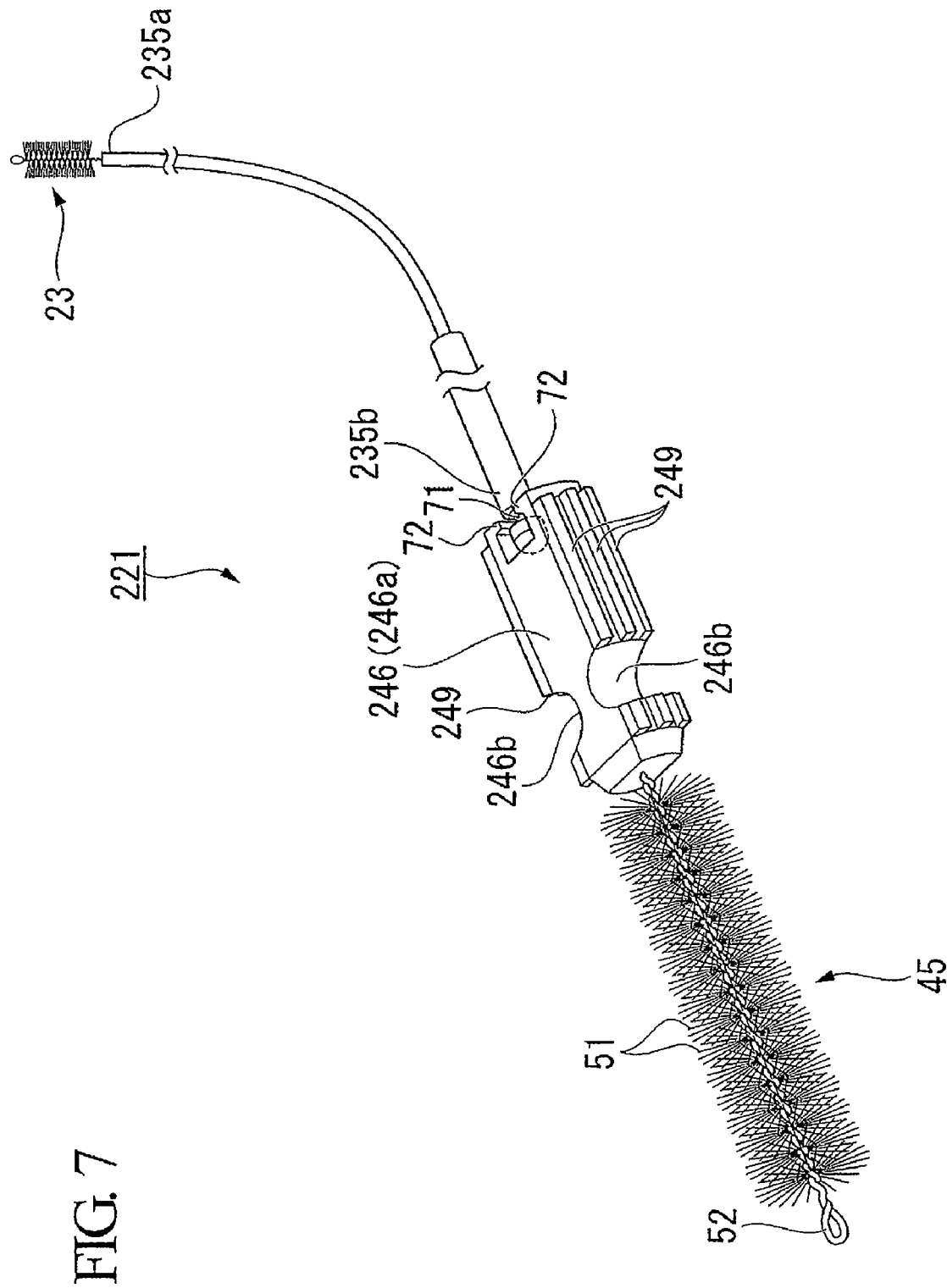
FIG. 7 is a perspective view illustrating a treatment tool according to a third embodiment of the present invention.
Figure 8:
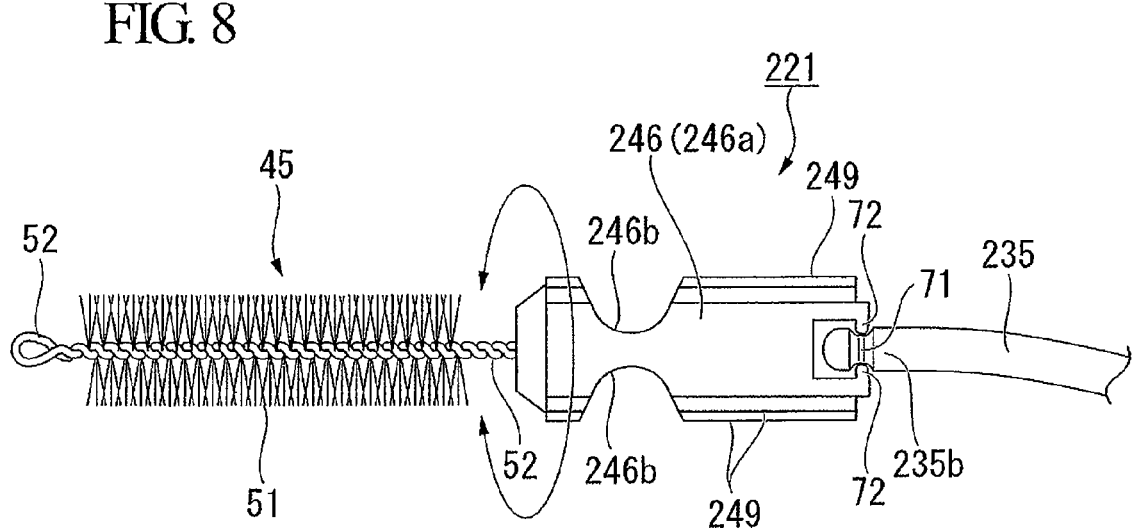
FIG. 8 is a side view illustrating a configuration of a part of the treatment tool.

As shown in FIG. 7, a portion on the side of the second terminal 235b of the elongated member 235 is thicker than a portion on the side of the first terminal 235a. In addition, as shown in FIG. 8, the outer peripheral surface of the second terminal 235b is provided with a contraction portion 71 that is smaller than the diameters of the other portions on the side of the second terminal 235b.

Figure 9:
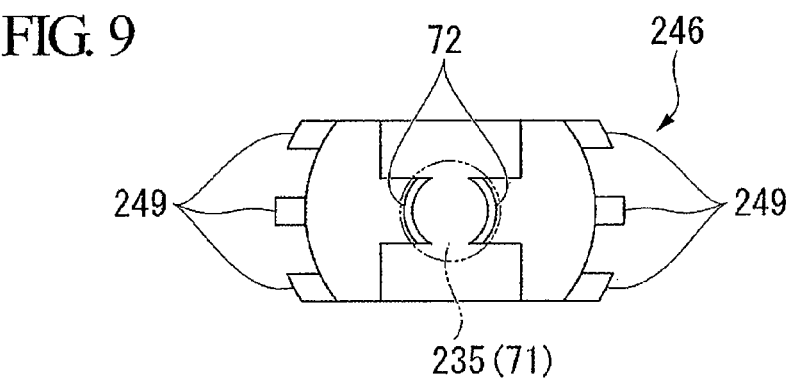
FIG. 9 is a front view illustrating a connection portion of the treatment tool.

Further, the connection portion 246 is provided with a support portion 72 instead of the rotation shaft 48 of the first embodiment. As shown in FIG. 9, the support portion 72 is formed in a curved shape that supports the contracted outer peripheral surfaces of the contraction portion 71 from the facing rear surfaces thereof. The contraction portion 71 and the support portion 72 are fitted to each other so as to be attachable to each other or detachable from each other in accordance with the relative movement in the radial direction.

Furthermore, the connection portion 246 includes a handle portion 246a corresponding to the above-described handle portion 46a, but a part of the outer peripheral surface of the handle portion 246a is provided with a pair of recess portions 246b that is formed in a recess shape in the radial direction.

In the treatment tool 221 of the embodiment, the elongated member 235 is rotatable about the axis of the elongated member 235 while being supported on the support portion 72. Accordingly, the rotation operations of the connection portion 246 and the elongated member 235 are not interlocked with each other. For this reason, even when the handle portion 246a is rotated while extraneous matter such as biological tissue adheres to the first body portion 23, it is possible to rotate the second body portion 45 without scattering the extraneous matter from the first body portion 23.

Further, since it is possible to suppress the forward/backward movement, that is, the sliding movement in the axial direction between the fingers and the handle portion by holding the recess portion 246b using his/her fingers, it is possible to further improve the workability.

Modified Example

Hereinafter, a modified example of the connection portion of the treatment tool of the embodiment will be described with reference to FIG. 10.

Figure 10:
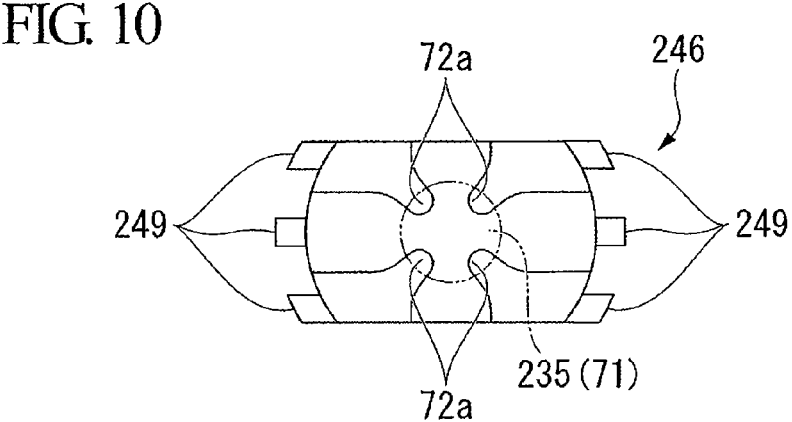
FIG. 10 is a diagram illustrating a modified example of the connection portion.

FIG. 10 is a diagram when the connection portion 246 is viewed from the elongated member 235 to the second body portion 45. As shown in FIG. 10, in the modified example, the connection portion 246 includes support portions 72a instead of the support portion 72. The support portions 72a are adapted to support the contraction portion 71 of the elongated member 235 at four points distanced from each other in the circumferential direction.

Likewise, even when the support portions 72a lock the contraction portion 71 of the elongated member 235 while coming into point contact therewith, the elongated member 235 is rotatable about the axis of the elongated member 235 while being supported on the support portions 72a in the same way as the above-described embodiments. Accordingly, even when the handle portion 246a is rotated while extraneous matter such as biological tissue adheres to the first body portion 23, it is possible to rotate the second body portion 45 without scattering the extraneous matter from the first body portion 23.

Fourth Embodiment

Next, a treatment tool according to a fourth embodiment of the present invention will be described with reference to FIGS. 11 and 12.

Figure 11:
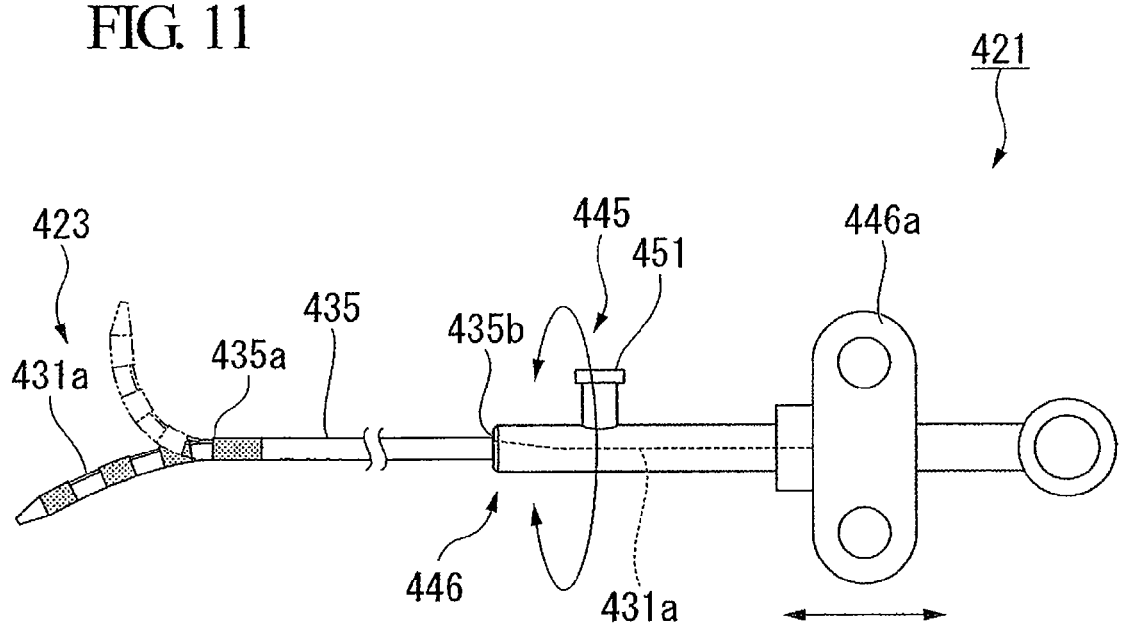
FIG. 11 is a plan view illustrating a treatment tool according to a fourth embodiment of the present invention.

As shown in FIG. 11, a treatment tool 421 of the embodiment is a treatment tool that includes a catheter 435 which is insertable into a body cavity instead of the elongated member 35 of the first embodiment. Further, the treatment tool 421 includes a first body portion 423 instead of the first body portion 23, a liquid supply opening metal 445 instead of the second body portion 45, and a connection portion 446 instead of the connection portion 46.

The catheter 435 includes a first terminal 435a and a second terminal 435b, and is a substantially tubular and flexible member that includes a lumen 435c (refer to FIG. 12) extending from the first terminal 435a to the second terminal 435b. The first terminal 435a of the catheter 435 is provided with a front end curving mechanism 423 as a first body portion.

Further, the front end curving mechanism 423 includes an angle wire 431a which is formed of a flexible wire, and an angle wire 431a is disposed so as to have a positional relationship in which the angle wire extends in the length direction along the outer peripheral surface of the front end curving mechanism 423. The angle wire 431a is fixed to the outer peripheral surface of the front end curving mechanism 423 at the front end of the front end curving mechanism 423, and is inserted and supported to the outer peripheral surface of the front end curving mechanism 423 so as to be movable forward or backward with a predetermined gap therebetween in the length direction. Further, the angle wire 431a is inserted through the inside of the wall portion of the catheter 435 so as to extend in the length direction toward the second terminal 435b.

Figure 12:
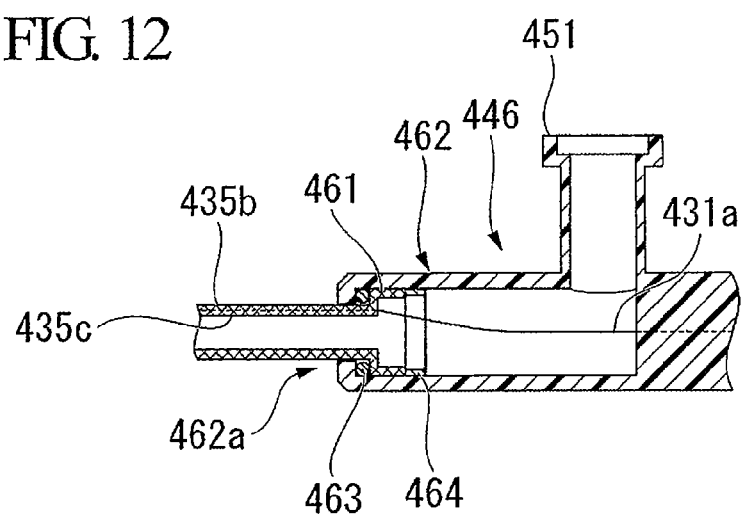
FIG. 12 is a cross-sectional view illustrating a connection portion of the treatment tool.

FIG. 12 is a cross-sectional view illustrating the connection portion 446. As shown in FIG. 12, the second terminal 435b is rotatably locked to the connection portion 446. The second terminal 435b is provided with a swollen portion 461 corresponding to the swollen portion 61 of the second embodiment. The swollen portion 461 is swelled from the outer peripheral surface of the catheter 435 to the outside of the radial direction so as to have an annular shape in cross-section in the radial direction. On the other hand, the connection portion 446 is provided with a support portion 462 that supports the second terminal 435b.

The support portion 462 is formed in a substantially tube shape so as to be covered by the outer periphery of the opening end portion of the second terminal 435b. Further, an opening end portion 462a as a front end of the support portion 462 protrudes inward in the radial direction, and the swollen portion 461 is adapted to be locked thereto.

In addition, a packing ring 463 and a stopper 464 formed of a flexible material such as rubber or silicone are interposed between the support portion 462 and the outer peripheral surface on the side of the second terminal 435b of the catheter 435, and the support portion 462 and the swollen portion 461 are disposed so as to be slidable about the axis of the catheter 435 and to be water-tightly connected to each other.

Further, the angle wire 431a is disposed at the connection portion 446 so as to extend coaxially with the catheter 435. The connection portion 446 is provided with a handle portion 446a which is used to move forward or backward the angle wire 431a in the axial direction relative to the catheter 435 (refer to FIG. 11).

Furthermore, in the connection portion 446, one end is opened to the side of the lumen 435c of the catheter 435 so as to communicate with the lumen 435c, and the other end is provided with the liquid supply opening metal 445 as the second body portion released to the outside.

Moreover, as shown in FIG. 11, the other end of the liquid supply opening metal 445 may be opened to the side of the connection portion 446, or may be opened to the outside along the axial direction of the catheter 435. The outer periphery 451 of the opening end portion of the other end of the liquid supply opening metal 445 has a known lure lock structure, which enables the water-tight connection to a syringe, a liquid supply pump, or the like. Likewise, the fluid conduit is formed from the liquid supply opening metal 445 to the front end curved portion 423 via the lumen 435c.

Besides, in the embodiment, since the rotation operations of the liquid supply opening metal 445 and the catheter 435 are not interlocked with each other, it is possible to freely rotate the liquid supply opening metal 445 about the axis of the catheter 435 while maintaining the curved state of the front end curved portion 423 using the angle wire 431a. Accordingly, since it is possible to rotate a syringe or the like attached to the liquid supply opening metal 445 to a desired position, it is possible to improve the operability of the treatment tool 421.

First Modified Example

Figure 13:
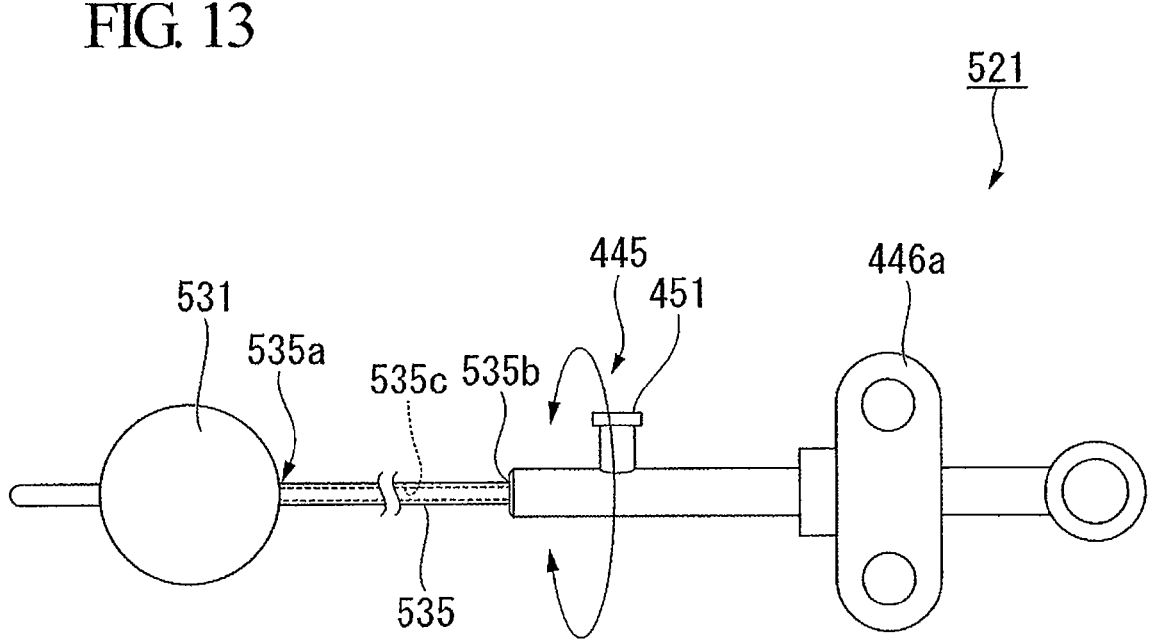
FIG. 13 is a plan view illustrating a modified example of the treatment tool.

Hereinafter, a modified example of the treatment tool of the embodiment will be described with reference to FIG. 13.

A treatment tool 521 of the modified example is a balloon catheter that includes a balloon 531 capable of being expanded or contracted instead of the first body portion 423. In addition, the treatment tool includes a catheter 535 instead of the catheter 435 and a lumen 535c of which the first terminal 535a is opened to the inside of the balloon 531 and which extends toward the second terminal 535b.

In the modified example, it is possible to rotate the liquid supply opening metal 445 about the axis of the catheter 535 by rotating the handle portion 446a about the axis of the catheter 535. Here, since the connection portion 446 and the catheter 535 are rotatably locked to each other at the connection portion 446, the rotation operations of the liquid supply opening metal 445 and the balloon 531 are not interlocked with each other.

Accordingly, it is possible to freely rotate the balloon 531 about the axis of the catheter 535 while maintaining the rotation position of the liquid supply opening metal 445 to a desired position. Therefore, it is possible to improve the operability of the treatment tool 521.

Fifth Embodiment

Next, a treatment tool according to a fifth embodiment of the present invention will be described with reference to FIGS. 14 and 15.

Figure 14:
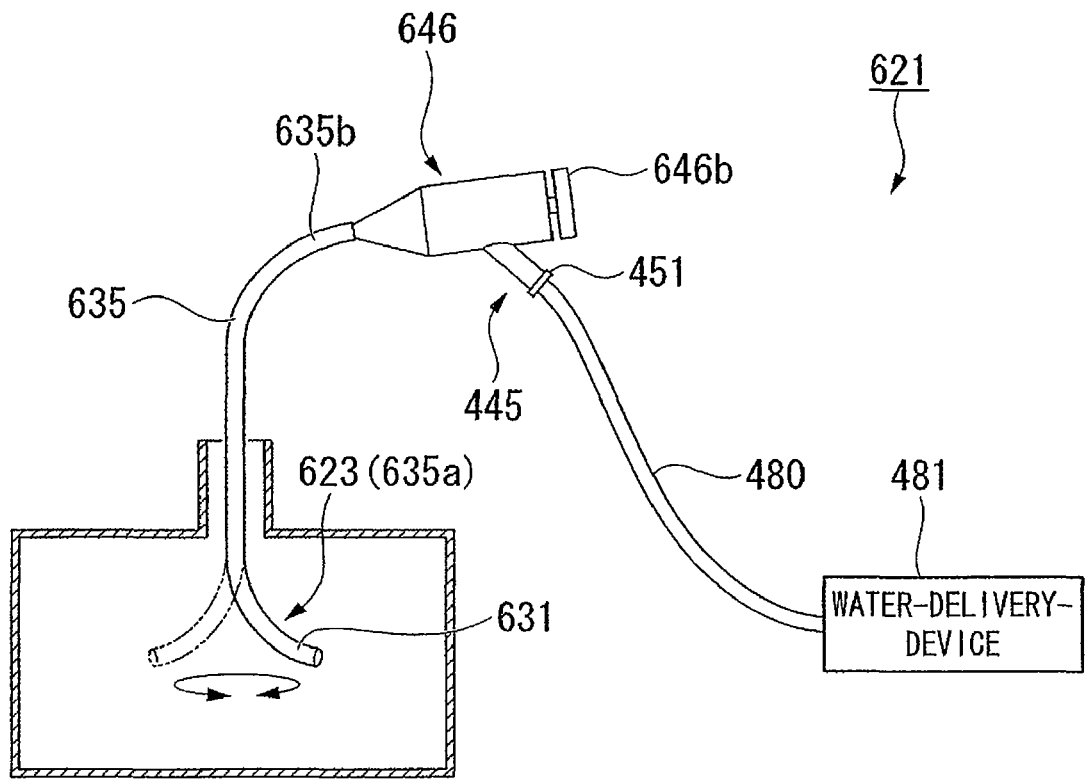
FIG. 14 is a plan view illustrating a treatment tool according to a fifth embodiment of the present invention.

As shown in FIG. 14, a treatment tool 621 of the modified example is a treatment tool that includes a liquid supply tube 635 insertable into a body cavity instead of the elongated member 35 of the first embodiment. In addition, the treatment tool 621 includes a first body portion 623 instead of the first body portion 23 and a connection portion 646 instead of the connection portion 46.

The first body portion 623 is provided with a front end curved portion 631 which is formed by curving the front end side thereof. In addition, the water supply opening metal 445 of the fourth embodiment is provided as the second body portion, and a tubular water supply cord 480 is attachably or detachably connected thereto.

Figure 15:
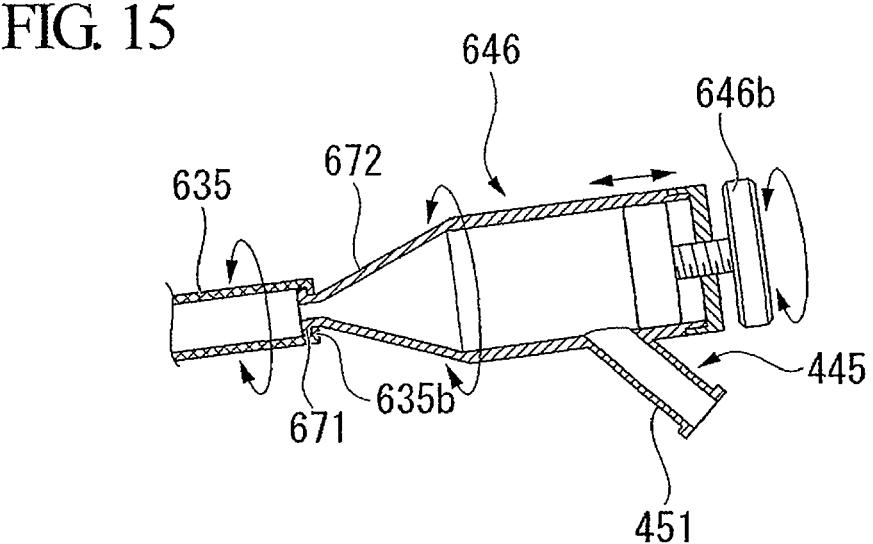
FIG. 15 is a cross-sectional view illustrating a connection portion of the treatment tool.

FIG. 15 is a cross-sectional view illustrating the connection portion 646. As shown in FIG. 15, the connection portion 646 is provided with a cock 646b that is used to select the communication or the interruption with the inside of the water supply opening metal 445. As the cock 646b, for example, a piston-shaped lid may be provided so as to block the inside of the water supply opening metal 445 as shown in FIG. 15.

In the embodiment, the tubular water supply cord 480 may be connected to the water supply opening metal 445, and a water supply mechanism 481 may be connected thereto so as to circulate the liquid inside the water supply cord 480. In addition, the liquid may be ejected from the front end of the tube 635 by circulating the liquid using the water supply mechanism 481. Further, the liquid may be supplied by connecting a syringe to the water supply opening metal 445.

While the preferred embodiments of the present invention have been described with reference to the drawings, the detailed configuration is not limited thereto, and the design may be modified within the scope of the spirit of the present invention.

For example, in the first embodiment of the present invention, the swollen portion 37 is formed by pressing the second terminal 35b of the elongated member 35, but the rigidity of the swollen portion 37 may be improved by folding back a part of the pressed second terminal 35b.

Further, the swollen portion 37 has a shape in which the maximum outer diameter of the swollen portion 37 is larger than the inner diameter of the rotation shaft 48. If the elongated member 35 is rotatable about the rotation shaft 48, the same effect as that of the present invention may be obtained even when any shape is adopted. For example, when a pin or E-ring is fixed to the second terminal 35b of the elongated member 35, it is possible to prevent the elongated member from being separated from the rotation shaft 48.

According to the treatment tool of the present invention, since the elongated member having the first body portion fixed thereto is rotatably locked to the connection portion, it is possible to further improve the workability of the treatment.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

The invention claimed is:

1. A treatment tool comprising:
   an elongated member which is formed of a flexible material and includes a first terminal and a second terminal;
   a first brush which is fixed to the first terminal so as to clean a target;
   a handle portion which is provided in the second terminal and is provided with a rotation shaft holding the elongated member so as to be rotatable about the axis of the elongated member; and
   a second brush fixed to the handle portion so as to clean the target and is rotated with the handle portion relative to the elongated member when rotating the handle member relative to the elongated member,
   wherein the second terminal is inserted into the rotation shaft and protrudes from the rotation shaft to an inner portion of the handle portion;
   wherein a swollen portion which is swelled in a radial direction of the elongated member is formed in the second terminal; and
   wherein an outer shape of the swollen portion is larger than an inner diameter of the rotation shaft.

2. The treatment tool according to claim 1,
   wherein the handle portion includes a concave portion to which the swollen portion is fitted so as to be rotatable about the axis.

3. The treatment tool according to claim 1,
   wherein the second terminal includes a contraction portion which is formed in a part of the outer peripheral surface of the second terminal so as to have a diameter smaller than those of the other portions, and
   wherein the handle portion includes a support portion which slidably engages with the contraction portion and supports the elongated member so as to be rotatable about the axis.

4. The treatment tool according to claim 1,
wherein the handle portion includes an expansion portion which is enlarged in the radial direction of the elongated member.

5. The treatment tool according to claim 1,
wherein the handle portion includes a convex protrusion portion which protrudes outward from the outer peripheral surface of the handle portion and extends in parallel to the axis.

6. The treatment tool according to claim 1,
   wherein the handle portion includes a grip surface which is formed in a part of the outer peripheral surface of the handle portion so as to be formed as a plane parallel to the axis.

* * * * *